United States Patent [19]

Butler

[11] Patent Number: 4,551,470

[45] Date of Patent: Nov. 5, 1985

[54] HEXAHYDRO-3,5-DIOXO-1H-PYRROLI-ZINE-2-CARBOXYLIC ACID AND DERIVATIVES, AND USE FOR REVERSING ELECTROCONVULSIVE SHOCK AMNESIA

[75] Inventor: Donald E. Butler, Ann Arbor, Mich.

[73] Assignee: Warner-Lambert Company, Morris Plains, N.J.

[21] Appl. No.: 527,718

[22] Filed: Aug. 29, 1983

[51] Int. Cl.[4] ..................... A61K 31/40; C07D 487/06
[52] U.S. Cl. .................................... 514/413; 548/453
[58] Field of Search ....................... 578/453; 424/274; 514/413

[56] References Cited

PUBLICATIONS

Hardegger et al., Helv., 38, p. 312 (1955).

Primary Examiner—Glennon H. Hollrah
Assistant Examiner—D. B. Springer
Attorney, Agent, or Firm—Jerry F. Janssen

[57] ABSTRACT

Hexahydro-3,5-dioxo-1H-pyrrolizine-2-carboxylic acid, its esters, ammonium, metal, and organic amine salts are useful for the treatment of senility, for enhancing memory, and for reversing electroconvulsive shock induced amnesia in humans. Pharmaceutical compositions including these compounds, and a method of treatment employing these pharmaceutical compositions is disclosed.

16 Claims, No Drawings

HEXAHYDRO-3,5-DIOXO-1H-PYRROLIZINE-2-CARBOXYLIC ACID AND DERIVATIVES, AND USE FOR REVERSING ELECTROCONVULSIVE SHOCK AMNESIA

BACKGROUND OF THE INVENTION

This invention relates to compounds and pharmaceutical compositions useful for treating patients suffering from senility and useful for enhancing memory and in the treatment of induced amnesia. More particularly, this invention concerns hexahydro-3,5-dioxo-1H-pyrrolizine-2-carboxylic acid, its esters and pharmaceutically acceptable salts, pharmaceutical compositions including these compounds, and a method of treating senility, for enhancing memory or of reversing electroconvulsive shock-induced amnesia in humans.

U.S. Pat. No. 4,372,966 to Butler assigned to the present assignee discloses pharmaceutical compositions including dihydro-1H-pyrrolizine-3,5(2H,6H)dione as a cognition activator.

The S-enantiomer of the ethyl ester of hexahydro-3,5-dioxo-1H-pyrrolizione-2-carboxylic acid was prepared by Hardegger and Ott in 1955 in their elucidation of the configuration of several derivatives of cocaine and ecgoninic acid (E. Hardegger and H. Ott, Helv. 38:312 (1955)).

SUMMARY OF THE INVENTION

In accordance with one aspect of the present invention, compounds useful for the treatment of senility, of enhancing memory, or for reversing electroconvulsive shock induced amnesia in humans possess the structural formula I

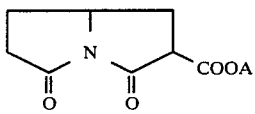

where A is hydrogen, methyl, alkyl of from three to six carbon atoms, phenyl, —(CH$_2$)$_{1-4}$phenyl, ammonium, or a cation derived from a pharmaceutically acceptable metal or organic amine.

In accordance with another aspect of the present invention, pharmaceutical compositions useful for the treatment of senility, of enhancing memory, or of reversing electroconvulsive shock induced amnesia in humans comprise an effective amount of a compound as defined above or hexahydro-3,5-dioxo-1H-pyrrolizine-2-carboxylic acid ethyl ester in combination with a pharmaceutically acceptable carrier.

In accordance with yet another aspect of the present invention, a method of the present invention, a method of treating senility, of enhancing memory, or of reversing electroconvulsive shock induced amnesia in humans comprises administering to a human an effective amount of a compound having the structural formula given above or hexahydro-3,5-dioxo-1H-pyrrolizine-2-carboxylic acid ethyl ester.

DETAILED DESCRIPTION

Compounds in accordance with the present invention are prepared by the reaction sequence illustrated in Reaction Scheme I below:

REACTION SCHEME I

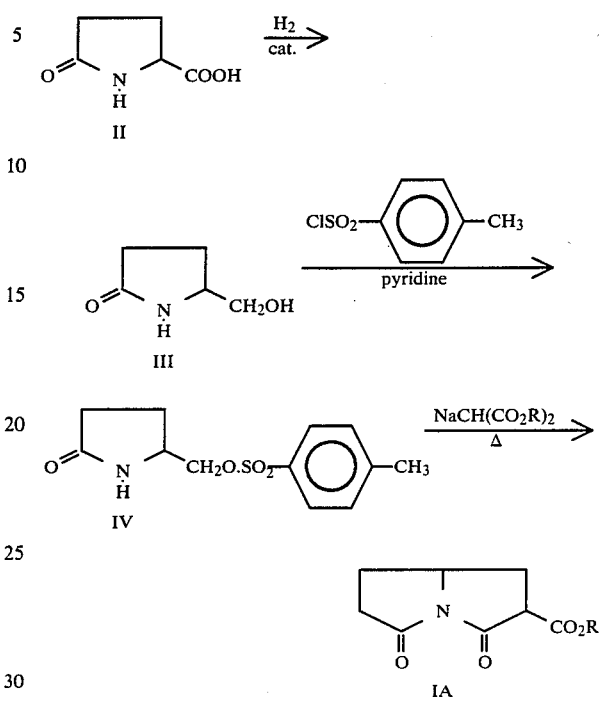

The individual stereoisomers of III can be prepared from the corresponding d- or l-acids as shown below.

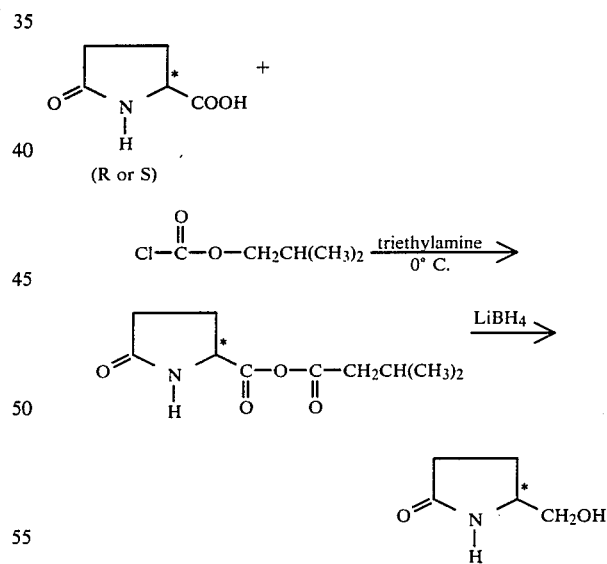

5-Oxo-proline (also known as pyroglutamic acid) (II) is reduced by hydrogen over palladium or platinum catalyst to produce the corresponding alcohol, d,l-2-oxo-5-hydroxymethylpyrrolidine (III). The alcohol (III) or the individual d- or l-isomers are reacted with p-toluenesulfonyl chloride, in the presence of a nitrogen base such as pyridine, to produce the tosylate (IV). The tosylate (IV) is reacted with the appropriate sodium dialkyl malonate salt in an inert solvent such as dry dioxane to produce esters in accordance with the present invention (IA).

The free acid (IB) is produced by catalytic hydrogenolysis of the benzyl ester (IC) or by hydrolysis of the t-butyl ester (D) in dilute aqueous acid solution.

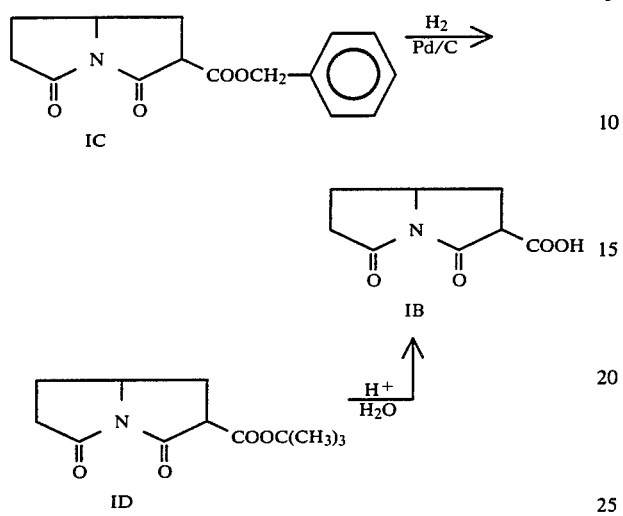

The starting material, II, for the reaction sequence illustrated in Reaction Scheme I, 5-oxo-proline, is prepared in accordance with the teachings of V. Skola in Z. Zucherind. czechoslov. Rep., 44:347–351 (1920) where preparation of the l, and d,l compounds from d-glutamic acid is described.

The free acid, (IB), is converted to a metal, ammonium, or organic amine salt, for example, by suspending the free acid in a suitable solvent such as water and adjusting the pH with a pharmaceutically acceptable metal base, ammonium hydroxide, or organic amine base, and then subsequently removing the solvent under reduced pressure. The free acid may be regenerated, if desired, by treating the salt form with an acid. For example, dilute aqueous hydrochloric acid may be utilized to regenerate the free form of the acid from particular salt. While the free acid form and the various salts vary somewhat from one another in their physical properties such as solubility in polar solvents, the free acid form and the various salts are considered equivalent for purposes of this invention.

By the term alkyl group is meant, throughout this specification and the appended claims, branched and unbranched saturated hydrocarbon groupings.

The term "pharmaceutically acceptable metal" cation contemplates the positively charged ions derived from such metals as sodium, potassium, magnesium, calcium, aluminum, zinc, iron, and the like.

The term "pharmaceutically acceptable amine" cation contemplates the positively charged ammonium ion and analogous ions derived from organic nitrogenous bases strong enough as bases to form salts with hexahydro-3,5-dioxo-1H-pyrrolizine-2-carboxylic acid.

Bases useful for the purpose of forming pharmaceutically acceptable nontoxic addition salts of hexahydro-3,5-dioxo-1H-pyrrolizine-2-carboxylic acid form a class whose limits are readily understood to those skilled in the art. For purposes of illustration, the class can be said to comprise, amine cations of the formula:

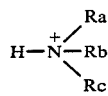

wherein Ra, Rb, and Rc, independently may be alkyl of from one to six carbon atoms, cycloalkyl of from about three to six carbon atoms, aryl, aralkyl of from about seven to about ten carbon atoms, hydroxyalkyl of from two to four carbon atoms, or monarylhydroxyalkyl of from about 8 to about 15 carbon atoms. Further, when taken together with the nitrogen atom to which they are attached, any tw of Ra, Rb, and Rc may form part of a 5-membered or 6-membered nitrogen heterocyclic aromatic or nonaromatic ring containing carbon or oxygen, said nitrogen heterocyclic rings being unsubstituted, monosubstituted or disubstituted with alkyl groups of from one to six carbon atoms.

Specific examples of organic amine cations contemplated as falling within the scope of the present invention include mono-, di-, and trimethylammonium, mono-, di-, and triethylammonium, mono-, di-, and tripropylammonium (n-propyl and iso-propyl), ethyldimethylammonium, benzylammonium, dibenzylammonium, benzyldimethylammonium, cyclohexylammonium, piperidinium, morpholinium, pyrrolidinium, 4-ethylmorpholinium, 1-isopropylpyrrolidinium, 1,4-dimethylpiperazinium, 1-n-butylpiperdinium, 2-methylpiperidinium, 1-ethyl-2-methylpiperidinium, mono-, di-, and triethanolammonium, ethyldiethanolammonium, n-butylmonoethanolammonium, tris(hydroxymethyl)methylammonium, phenylmonoethanolammonium, and the like. Hexahydro-3,5-dioxo-1H-pyrrolizine-2-carboxylic acid and the various salts of that acid as defined above can exist in the unsolvated form as well as solvated forms, including hydrates, alcoholates such as solvates with ethanol and similar alcohols, or solvates with other pharmaceutically acceptable, nontoxic solvents. In general, the solvated forms of the compounds of this invention are considered equivalent to the unsolvated forms for the purposes of this invention.

Hexahydro-3,5-dioxo-1H-pyrrolizine-2-carboxylic acid and its derivative esters and salts possess asymmetric carbon atoms at the positions marked by the asterisks in the structural formula give below, and thus either center may exist in the R or S form. The present invention contemplates the pure R,R form of the free acid, its esters and salts, the pure S,S form, the pure S,R form, the pure R,S form, or mixtures including the racemic mixture, as falling within the scope of the invention.

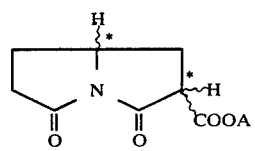

Spceific compounds contemplated as falling within the scope of the present invention include hexahydro-3,5-dioxo-1H-pyrrolizine-2-carboxylic acid and its esters, ammonium and metal and amine salts including, by way of illustrative example, the following:

Hexahydro-3,5-dioxo-1H-pyrrolizine-2-carboxylic acid methyl ester.

Hexahydro-3,5-dioxo-1H-pyrrolizine-2-carboxylic acid n-propyl ester.
Hexahydro-3,5-dioxo-1H-pyrrolizine-2-carboxylic acid n-butyl ester.
Hexahydro-3,5-dioxo-1H-pyrrolizine-2-carboxylic acid 1,1-dimethylethyl ester.
Hexahydro-3,5-dioxo-1H-pyrrolizine-2-carboxylic acid n-pentyl ester.
Hexahydro-3,5-dioxo-1H-pyrrolizine-2-carboxylic acid 2-methylbutyl ester.
Hexahydro-3,5-dioxo-1H-pyrrolizine-2-carboxylic acid n-hexyl ester.
Hexahydro-3,5-dioxo-1H-pyrrolizine-2-carboxylic acid 3-methylpentyl ester.
Hexahydro-3,5-dioxo-1H-pyrrolizine-2-carboxylic acid 2-methyl-3-pentyl ester.
Hexahydro-3,5-dioxo-1H-pyrrolizine-2-carboxylic acid phenylmethyl ester.
Hexahydro-3,5-dioxo-1H-pyrrolizine-2-carboxylic acid 2-phenylethyl ester.
Hexahydro-3,5-dioxo-1H-pyrrolizine-2-carboxylic acid 3-phenylpropyl ester.
Hexahydro-3,5-dioxo-1H-pyrrolizine-2-carboxylic acid 4-phenylbutyl ester.
Hexahydro-3,5-dioxo-1H-pyrrolizine-2-carboxylic acid sodium salt.
Hexahydro-3,5-dioxo-1H-pyrrolizine-2-carboxylic acid potassium salt.
Hexahydro-3,5-dioxo-1H-pyrrolizine-2-carboxylic acid magnesium salt.
Hexahydro-3,5-dioxo-1H-pyrrolizine-2-carboxylic acid calcium salt.
Hexahydro-3,5-dioxo-1H-pyrrolizine-2-carboxylic acid ammonium salt.
Hexahydro-3,5-dioxo-1H-pyrrolizine-2-carboxylic acid methyl ammonium salt.
Hexahydro-3,5-dioxo-1H-pyrrolizine-2-carboxylic acid dimethylammonium salt.
Hexahydro-3,5-dioxo-1H-pyrrolizine-2-carboxylic acid trimethylammonium salt.
Hexahydro-3,5-dioxo-1H-pyrrolizine-2-carboxylic acid ethylammonium salt.
Hexahydro-3,5-dioxo-1H-pyrrolizine-2-carboxylic acid diethylammonium salt.
Hexahydro-3,5-dioxo-1H-pyrrolizine-2-carboxylic acid triethylammonium salt.
Hexahydro-3,5-dioxo-1H-pyrrolizine-2-carboxylic acid tri-n-propylammonium salt.
Hexahydro-3,5-dioxo-1H-pyrrolizine-2-carboxylic acid piperidinium salt.
Hexahydro-3,5-dioxo-1H-pyrrolizine-2-carboxylic acid morpholinium salt.
Hexahydro-3,5-dioxo-1H-pyrrolizine-2-carboxylic acid pyrrolidinium salt.
Hexahydro-3,5-dioxo-1H-pyrrolizine-2-carboxylic acid piperazinium salt.
Hexahydro-3,5-dioxo-1H-pyrrolizine-2-carboxylic acid monoethanolammonium salt.
Hexahydro-3,5-dioxo-1H-pyrrolizine-2-carboxylic acid diethanolammonium salt.
Hexahydro-3,5-dioxo-1H-pyrrolizine-2-carboxylic acid triethanolammonium salt.
Hexahydro-3,5-dioxo-1H-pyrrolizine-2-carboxylic acid tris(hydroxymethyl)methylammonium salt.
Hexahydro-3,5-dioxo-1H-pyrrolizine-2-carboxylic acid benzylammonium salt.
Hexahydro-3,5-dioxo-1H-pyrrolizine-2-carboxylic acid phenylmonoethanolammonium salt.

Compounds in accordance with this invention are effective in treating senility, in enhancing memory, or of reversing the effects of electroconvulsive shock-induced amnesia. The effectiveness of these compounds is determined by the test designed to show the compound's ability to reverse amnesia produced by electroconvulsive shock. The test is more fully described in U.S. Pat. No. 4,145,347, issued Mar. 20, 1979, the disclosure of which is herein incorporated by reference. The only deviation in the present invention is that the compounds tested are administered orally, and the duration of the electroconvulsive shock administered in 1.0 seconds.

Employing this test, the following criteria are used in interpreting the percent of amnesia reversal scores: 40 percent or more amnesia reversal (active=A), 25 to 39 percent amnesia reversal (borderline activity=C), and 0 to 25 percent amnesia reversal (inactive=N).

The Table below illustrates amnesia reversal of hexahydro-3,5-dioxo-1H-pyrrolizine-2-carboxylic acid ethyl ester when orally administered to standard experimental laboratory animals in the above-referenced test.

TABLE

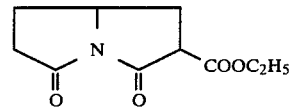

| | mg/kg | |
|---|---|---|
| 1 | 10 | 100 |
| % amnesia reversal  10 | 82 (A) | 0 |

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active (with or without other carriers) is surrounded by carrier, which is thus in association with it.

Similarly, cachets are included. Tablets, powders, cachets, and capsules can be used as solid dosage forms suitable for oral administration.

For preparing suppositiories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as cognition activators, the mammalian dosage range for a 70 kg subject is from 1 to 1500 mg/kg of body weight per day or preferably 25 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

To enable one skilled in the art to practice the present invention, the following illustrative examples are provided. These examples should not be viewed, however, as limiting the scope of the present invention as defined by the appended claims, but as merely illustrative thereof.

EXAMPLE 1

Preparation of hexahydro-3,5-dioxo-1H-pyrrolizine-2-carboxylic acid ethyl ester

A solution of diethyl malonate (45 ml, 47.5 g, 0.3 mole) in dioxane (100 ml) is treated with sodium hydride (50% in mineral oil, 6.2 g, 0.129 mole) with stirring. After the hydrogen gas evolution subsides, a solution of d,l-5-tosylmethyl-2-oxo-pyrrolidine (16.1 g, 0.06 mole) (mp 128°–129° C. Lit. mp 130° C. Reference 1) in dioxane (200 ml) is added. The mixture is stirred and refluxed for six hours, cooled, and filtered. The filtrate is concentrated at reduced pressure, dissolved in chloroform (200 ml) and washed with water (5 ml). The chloroform layer is dried (MgSO$_4$), filtered, and concentrated at reduced pressure to remove most unreacted diethyl malonate, finally at 0.1 mm and 80° C. to yield hexahydro-3,5-dioxo-1H-pyrrolizine-2-carboxylic acid ethyl ester as an oil. The oil is further purified by flash chromatography over silica (elution with 20:1 dichloromethane:methanol). After concentration of the desired fractions, the oil is heated at 100° C. and 0.1 mm pressure for 16 hour. Upon cooling, the pure hexahydro-3,5-dioxo-1H-pyrrolizine-2-carboxylic acid ethyl ester crystallizes; mp 65°–67° C.

EXAMPLE 2

Preparation of hexahydro-3,5-dioxo-1H-pyrrolizine-2-carboxylic acid benzyl ester A solution of dibenzyl malonate (56.8 g, 0.2 mole) in dioxane (100 ml) is treated with sodium hydride (50% in mineral oil, 6.2 g, 0.129 mole) with stirring. After the hydrogen gas evolution subsides, a solution of d,l-5-tosylmethyl -2-oxo-pyrrolidine (16.1 g, 0.06 mole) in dioxane (200 ml) is added. The mixture is stirred and refluxed for six hours, cooled, and filtered. The filtrate is concentrated at reduced pressure, dissolved in chloroform (200 ml) and washed with water (5 ml). The chloroform layer is dried MgSO$_4$), filtered, and concentrated at reduced pressure finally at 0.1 ml and 80° C. to remove most unreacted dibenzyl malonate to yield hexahydro-3,5-dioxo-1H-pyrrolizine-2-carboxylic acid benzyl ester as an oil. The oil is further purified by flash chromatrograpy over silica (elution with 20:1 dichloromethane:methanol. After concentration of the desired fractions, the oil is heated at 100° C. and 0.1 mm pressure for 16 hours to yield upon cooling, the pure hexahydro-3,5-dioxo-1H-pyrrolizine-2-carboxylic acid benzyl ester.

EXAMPLE 3

Preparation of hexahydro-3,5-dioxo-1H-pyrrolizine-2-carboxylic acid

A solution of hexahydro-3,5-dioxo-1H-pyrrolizine-2-carboxylic acid benzyl ester 25.90.1 g, yy mole) in dioxane (200 ml) is treated with hydrogen gas in the presence of 20% Pd/C catalyst for eight hours. The mixture is filtered and concentrated at reduced pressure (below 25° C.) to yield pure hexahydro-3,5-dioxo-1H-pyrrolizine-2-carboxylic acid.

EXAMPLE 4

Preparation of hexahydro-3,5-dioxo-1H-pyrrolizine-2-carboxylic acid sodium salt A solution of hexahydro-3,5-dioxo-1H-pyrrolizine-2-carboxylic acid (18.3 g, 0.1 mole) in dioxane (200 ml) at 0° C. is treated with 0.1N sodium hydroxide solution (100 ml, 0.1 mole) and the resulting solution of the sodium salt of hexahydro-3,5-dioxo-1H-pyrrolizine-2-carboxylic acid is concentrated at reduced pressure to yield the dry sodium salt of hexahydro-3,5-dioxo-1H-pyrrolizine-2-carboxylic acid.

EXAMPLE 5

Preparation of hexahydro-3,5-dioxo-1H-pyrrolizine-2-carboxylic acid, potassium salt A solution of hexahydro-3,5-dioxo-1H-pyrrolizine-2-carboxylic acid, (18.3 g, 0.1 mole) in dioxane (200 ml) at 0° C. is treated with 0.1N potassium hydroxide solution (100 ml, 0.1 mole) and the resulting solution of the potassium salt of hexahydro-3,5-dioxo-1H-pyrrolizine-2-carboxylic acid is concentrated at reduced pressure to yield the dry potassium salt of hexahydro-3,5-dioxo-1H-pyrrolizine-2-carboxylic acid.

EXAMPLE 6

Preparation of hexahydro-3,5-dioxo-1H-pyrrolizine-2-carboxylic acid calcium salt A solution of hexahydro-3,5-dioxo-1H-pyrrolizine-2-carboxylic acid (8.3 g, 0.1 mole) in dioxane (200 ml) at 0° C. is treated with 0.1N calcium hydroxide solution (100 ml, 0.1 mole) and the resulting solution of the calcium salt of hexahydro-3,5-dioxo-1H-pyrrolizine-2-carboxylic acid is concentrated at reduced pressure to yield the dry calcium salt of hexahydro-3,5-dioxo-1H-pyrrolizine-2-carboxylic acid.

EXAMPLE 7

Preparation of hexahydro-3,5-dioxo-1H-pyrrolizine-2-carboxylic acid ammonium salt A solution of hexahydro-3,5-dioxo-1H-pyrrolizine-2-carboxylic acid (18.3 g, 0.1 mole) in dioxane (200 ml) at 0° C. is treated with 0.1N ammonium hydroxide solution (100 ml, 0.1 mole) and the resulting solution of the ammonium salt of hexahydro-3,5-dioxo-1H-pyrrolizine-2-carboxylic acid is concentrated at reduced pressure to yield the dry ammonium salt of hexahydro-3,5-dioxo-1H-pyrrolizine-2-carboxylic acid.

FORMULATION EXAMPLE 1

| Ingredient | Quantity |
| --- | --- |
| Hexahydro-3,5-dioxo-1H—pyrrolizine-2-carboxylic acid sodium salt | 161 g |
| Lactose | 1113 g |
| Corn Starch | 39 g |
| Hydroxypropyl cellulose | 30 g |
| Magnesium stearate | 7 g |
| Ethanol-water 50:50 | q.s. |

The hexahydro-3,5-dioxo-1H-pyrrolizine-2-carboxylic acid, sodium salt, lactose and hydroxypropyl cellulose are blended and granulated with 50:50 ethanol-water. The wet granulation is screened, dried, and rescreened. The resulting dried granulation is blended with the corn starch and the magensium stearate, and the mixture is compressed into 225 mg tablets using 11/32 inch standard concave punches. Yield equals approximately 6,000 tablets, each containing 26.9 mg of hexahydro-3,5-dioxo-1H-pyrrolizine-2-carboxylic acid, sodium salt equivalent to 25 mg of hexahydro-3,5-dioxo-1H-pyrrolizine-2-carboxylic acid.

By substituting an equivalent of another pharmaceutically acceptable salt of hexahydro-3,5-dioxo-1H-pyrrolizine-2-carboxylic acid for the hexahydro-3,5-dioxo-1H-pyrrolizine-2-carboxylic acid, sodium salt and adjusting the amount of lactose to give the same total weight in the above formula, there are again obtained 225 mg tablets each containing the equivalent of 25 mg of hexahydro-3,5-dioxo-1H-pyrrolizine-2-carboxylic acid.

FORMULATION EXAMPLE 2

| Ingredient | Quantity |
| --- | --- |
| Hexahydro-3,5-dioxo-1H—pyrrolizine-2-carboxylic acid calcium salt | 681.6 g |
| Lactose | 1437.4 g |
| Corn Starch | 60 g |
| Hydroxypropyl cellulose | 60 g |
| Magnesium stearate | 11 g |
| Ethanol-water 50:50 | q.s. |

The hexahydro-3,5-dioxo-1H-pyrrolizine-2-carboxylic acid, calcium salt, lactose and hydroxypropyl cellulose are blended and granulated with 50:50 ethanol-water. The wet granulation is screened, dried and rescreened. The resulting dried granulation is blended with the corn starch and the magensium stearate, and the mixture is compressed into 375 mg tablets using 13/32 inch standard concave punches. Yield equals approximately 6,000 tablets, each containing 113.6 mg of hexahydro-3,5-dioxo-1H-pyrrolizine-2-carboxylic acid, calcium salt equivalent to 100 mg of hexahydro-3,5-dioxo-1H-pyrrolizine-2-carboxylic acid.

By substituting an equivalent of another pharmaceutically acceptable salt of hexahydro-3,5-dioxo-1H-pyrrolizine-2-carboxylic acid for the hexahydro-3,5-dioxo-1H-pyrrolizine-2-carboxylic acid, calcium salt and adjusting the amount of lactose to give the same total weight in the above formula, there are again obtained 375 mg tablets each containing the equivalent of 100 mg of hexahydro-3,5-dioxo-1H-pyrrolizine-2-carboxylic acid.

FORMULATION EXAMPLE 3

| Ingredient | Quantity |
| --- | --- |
| Hexahydro-3,5-dioxo-1H—pyrrolizine-2-carboxylic acid calcium salt | 1696.8 g |
| Lactose | 1105.2 g |
| Corn Starch | 90 g |
| Hydroxypropyl cellulose | 90 g |
| Magnesium stearate | 18 g |
| Ethanol-water 50:50 | q.s |

The hexahydro-3,5-dioxo-1H-pyrrolizine-2-carboxylic acid, calcium salt, lactose and hydroxypropyl cellulose are blended and granulated with 50:50 ethanol-water. The wet granulation is screened, dried, and re-screened. The resulting dried granulation is blended with the corn starch and the magnesium stearate, and the mixture is compressed into 500 mg tablets using ½ inch standard concave punches. Yield equals approximately 6,000 tablets, each containing 282.8 mg of hexahydro-3,5-dioxo-1H-pyrrolizine-2-carboxylic acid, potassium salt equivalent to 250 mg of hexahydro-3,5-dioxo-1H-pyrrolizine-2-carboxylic acid.

By substituting an equivalent of another pharmaceutically acceptable salt of hexahydro-3,5-dioxo-1H-pyrrolizine-2-carboxylic acid for the hexahydro-3,5-dioxo-1H-pyrrolizine-2-carboxylic acid, potassium salt and adjusting the amount of lactose to give the same total weight in the above formula, there are again obtained 500 mg tablets each containing the equivalent of 250 mg of hexahydro-3,5-dioxo-1H-pyrrolizine-2-carboxylic acid.

FORMULATION EXAMPLE 4

| Ingredient | Quantity |
| --- | --- |
| Hexahydro-3,5-dioxo-1H—pyrrolizine-2-carboxylic acid Sodium salt | 269 g |
| Lactose | 1707 g |
| Magnesium stearate | 27 g |

The hexahydro-3,5-dioxo-1H-pyrrolizine-2-carboxylic acid, sodium salt, lactose, and magnesium stearate are blended and filled into Number 4 hard gelatin capsules, filling each capsule with 200 mg of the powder mixture. Yield equals approximately 10,000 capsules, each containing 26.9 mg of hexahydro-3,5-dioxo-1H-pyrrolizine-2-carboxylic acid, sodium salt equivalent to 25 mg of hexahydro-3,5-dioxo-1H-pyrrolizine-2-carboxylic acid.

By substituting an equivalent of another pharmaceutically acceptable salt of hexahydro-3,5-dioxo-1H-pyrrolizine-2-carboxylic acid for the hexahydro-3,5-dioxo-1H-pyrrolizine-2-carboxylic acid, sodium salt and adjusting the amount of lactose to give the same total weight in the above formula, there are again obtained 200 mg capsules each containing the equivalent of 25 mg of hexahydro-3,5-dioxo-1H-pyrrolizine-2-carboxylic acid.

FORMULATION EXAMPLE 5

| Ingredient | Quantity |
| --- | --- |
| Hexahydro-3,5-dioxo-1H—pyrrolizine-2-carboxylic acid Sodium salt | 1136 g |
| Lactose | 1976 g |
| Magnesium stearate | 68 g |

The hexahydro-3,5-dioxo-1H-pyrrolizine-2-carboxylic acid, calcium salt, lactose, and magnesium stearate are blended and filled into Number 2 hard gelatin capsules, filling each capsule with 200 mg of the powder mixture. Yield equals approximately 10,000 capsules, each containing 113.6 mg of hexahydro-3,5-dioxo-1H-pyrrolizine-2-carboxylic acid, calcium salt equivalent to 100 mg of hexahydro-3,5-dioxo-1H-pyrrolizine-2-carboxylic acid.

By substituting an equivalent of another pharmaceutically acceptable salt of hexahydro-3,5-dioxo-1H-pyrrolizine-2-carboxylic acid for the hexahydro-3,5-dioxo-1H-pyrrolizine-2-carboxylic acid, calcium salt and adjusting the amount of lactose to give the same total weight in the above formula, there are again obtained 200 mg capsules each containing the equivalent of 100 mg of hexahydro-3,5-dioxo-1H-pyrrolizine-2-carboxylic acid.

FORMULATION EXAMPLE 6

| Ingredient | Quantity |
| --- | --- |
| Hexahydro-3,5-dioxo-1H—pyrrolizine-2-carboxylic acid Sodium salt | 2828 g |
| Lactose | 2802 g |
| Magnesium stearate | 170 g |

The hexahydro-3,5-dioxo-1H-pyrrolizine-2-carboxylic acid, potassium salt, lactose, and magnesium stearate are blended and filled into Number 4 hard gelatin capsules, filling each capsule with 580 mg of the powder mixture. Yield equals approximately 10,000 capsules, each containing 282.8 mg of hexahydro-3,5-dioxo-1H-pyrrolizine-2-carboxylic acid, potassium salt equivalent to 250 mg of hexahydro-3,5-dioxo-1H-pyrrolizine-2-carboxylic acid.

By substituting an equivalent of another pharmaceutically acceptable salt of hexahydro-3,5-dioxo-1H-pyrrolizine-2-carboxylic acid for the hexahydro-3,5-dioxo-1H-pyrrolizine-2-carboxylic acid, potassium salt and adjusting the amount of lactose to give the same total weight in the above formula, there are again obtained 580 mg capsules each containing the equivalent of 250 mg of hexahydro-3,5-dioxo-1H-pyrrolizine-2-carboxylic acid.

I claim:

1. A compound having the formula

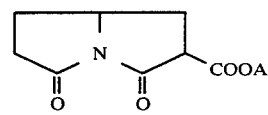

where A is hydrogen, methyl, alkyl of from three to six carbon atoms, phenyl, —(CH$_2$)$_{1-4}$phenyl, sodium, potassium, magnesium, calcium, aluminum, zinc, iron, or ammonium.

2. A compound in accordance with claim 1 wherein A is hydrogen, methyl, alkyl of from three to six carbon atoms, phenyl, or —(CH$_2$)$_{1-4}$phenyl.

3. A compound in accordance with claim 1 wherein A is selected from sodium, potassium, magnesium, calcium, aluminum, zinc, or iron.

4. A compound in accordance with claim 1 having the name hexahydro-3,5-dioxo-1$\underline{\text{H}}$-pyrrolizine-2-carboxylic acid.

5. A compound in accordance with claim 1 having the name hexahydro-3,5-dioxo-1$\underline{\text{H}}$-pyrrolizine-2-carboxylic acid methyl ester.

6. A compound in accordance with claim 2 having the name hexahydro-3,5-dioxo-1$\underline{\text{H}}$-pyrrolizine-2-carboxylic acid t-butyl ester.

7. A compound in accordance with claim 2 having the name hexahydro-3,5-dioxo-1$\underline{\text{H}}$-pyrrolizine-2-carboxylic acid benzyl ester.

8. A compound in accordance with claim 3 having the name hexahydro-3,5-dioxo-1$\underline{\text{H}}$-pyrrolizine-2-carboxylic acid sodium salt.

9. A compound in accordance with claim 3 having the name hexahydro-3,5-dioxo-1$\underline{\text{H}}$-pyrrolizine-2-carboxylic acid potassium salt.

10. A compound in accordance with claim 3 having the name hexahydro-3,5-dioxo-1$\underline{\text{H}}$-pyrrolizine-2-carboxylic acid magnesium salt.

11. A compound in accordance with claim 3 having the name hexahydro-3,5-dioxo-1$\underline{\text{H}}$-pyrrolizine-2-carboxylic acid calcium salt.

12. A compound in accordance with claim 1 having the name hexahydro-3,5-dioxo-1$\underline{\text{H}}$-pyrrolizine-2-carboxylic acid ammonium salt.

13. A pharmaceutical composition useful for the treatment of electroconvulsive shock induced amnesia in humans comprising an effective amount of a compound in accordance with claim 1 in combination with a pharmaceutically acceptable carrier.

14. A pharmaceutical composition useful for the treatment of electroconvulsive shock induced amnesia in humans comprising an effective amount of hexahydro-3,5-dioxo-1$\underline{\text{H}}$-pyrrolizine-2-carboxylic acid ethyl ester in combination with a pharmaceutically acceptable carrier.

15. A method of reversing amnesia caused by electroconvulsive shock in humans which comprises administering to said human an effective amount of a compound in accordance with claim 1.

16. A method of reversing amnesia caused by electroconvulsive shock in humans which comprises administering to said human an effective amount of hexahydro-3,5-dioxo-1$\underline{\text{H}}$-pyrrolizine-2-carboxylic acid ethyl ester.

* * * * *